United States Patent [19]

Mavunkel et al.

[11] Patent Number: 5,610,142
[45] Date of Patent: Mar. 11, 1997

[54] BRADYKININ ANTAGONIST PSEUDOPEPTIDE DERIVATIVES OF SUBSTITUTED 4-KETO-1,3,8-TRIAZASPIRO[4.5] DECAN-3-ALKANOIC ACIDS

[75] Inventors: Babu J. Mavunkel, Baltimore, Md.; Zhijian Lu, Scotch Plains, N.J.; Donald J. Kyle, Abingdon, Md.

[73] Assignee: Scios Inc., Mountain View, Calif.

[21] Appl. No.: 416,524

[22] Filed: Apr. 3, 1995

Related U.S. Application Data

[63] Continuation of Ser. No. 118,558, Sep. 9, 1993, abandoned, which is a continuation-in-part of Ser. No. 957,879, Oct. 8, 1992, Pat. No. 5,521,158.

[51] Int. Cl.$^6$ .................................................. A61K 38/08
[52] U.S. Cl. ............................... 514/16; 514/15; 514/17; 530/314; 530/328
[58] Field of Search ............................. 514/15, 16, 17; 530/314, 328

[56] References Cited

U.S. PATENT DOCUMENTS

| | | | |
|---|---|---|---|
| 4,242,329 | 12/1980 | Claeson et al. | 424/177 |
| 4,483,850 | 11/1984 | Patchett et al. | 424/177 |
| 4,693,993 | 9/1987 | Stewart et al. | 514/14 |
| 4,801,613 | 1/1989 | Stewart et al. | 514/14 |
| 4,822,894 | 4/1989 | Geiger et al. | 548/252 |
| 4,923,963 | 5/1990 | Stewart et al. | 530/314 |

FOREIGN PATENT DOCUMENTS

| | | | |
|---|---|---|---|
| 0334685 | 9/1989 | European Pat. Off. | |
| 370453 | 5/1990 | European Pat. Off. | C07K 7/18 |
| 413277 | 2/1991 | European Pat. Off. | C07K 7/18 |
| WO94/08607 | 4/1994 | WIPO. | |

OTHER PUBLICATIONS

Karanewsky et al., "(Phosphinyloxy)acyl Amino Acid Inhibitors of Angiotensin Converting Enzyme. 2. Terminal Amino Acid Analogues of (S)–1–[6–Amino–2–[[hydroxy(4–phenylbutyl)phosphinyl]oxy]–1–oxohexyl]–L–proline," Journal of Medicinal Chemistry, vol. 33, No. 5 (1990), pp. 1459–1469.
Smith et al., "Synthesis and Pharmacological Activity of Angiotensin Converting Enzyme Inhibitors: N–(Mercaptoacyl)–4–substituted–(S)–prolines," Journal of Medicinal Chemistry, vol. 31, No. 4 (1988), pp. 875–885.
Krapcho et al., "Angiotensin–Converting Enzyme Inhibitors. Mercaptan, Carboxyalkyl Dipeptide, and Phosphinic Acid Inhibitors Incorporating 4–Substituted Prolines," Journal of Medicinal Chemistry, vol. 31, No. 6 (1988), pp. 1148–1160.
Hock et al., "Hoe 140 A New Potent and Long Acting Bradykinin–Antagonist: in vitro studies", Br. J. Pharmacol., vol. 102, pp. 769–774 (1991).
Wirth et al., "Hoe 140 A New Potent and Long Acting Bradykinin–Antagonist: in vivo studies", Br. J. Pharmacol., vol. 102, pp. 774–777 (1991).

Pongracic et al., "A Competitive Kinin Receptor Antagonist, [DArg$^0$, Hyp$^3$, DPhe$^7$]–Bradykinin, Does Not Affect the Response to Nasal Provocation With Bradykinin", Br. J. Pharmacol., vol. 31, pp. 287–294 (1991).
Higgins et al., "A Study of the Efficacy of the Bradykinin Antagonist NPC567, in Rhinovirus infections in Human Volunteers", Chemical Abstracts #114: 220805d (1991).
Soler et al., "A Bradykinin Antagonist Modifies Antigen–Induced Airway Hyper–Responsiveness and Airway Inflammation in Allergic Sheep", Am. Rev. Respir. Dis. A327 (1989).
John M. Stewart, "Hydroxyproline Analogs of Bradykinin" Journal of Medicinal Chemistry (1974) vol. 17, No. 5 pp. 537–539.
J. M. Stewart, "Chemistry and Biologic Activity of Peptides Related to Bradykinin" Handbook of Experimental Pharamcol. vol. XXV Supp. Springer–Verlag Berlin Heidelberg NY (1979).
J. Barabe et al. "New Agonist and Antagonist Analogues of Bradykinin", Can. J. Physiol. Pharmacol., vol. 62, 1984 pp. 627–629.
Raymond J. Vavrek, et al., "Smooth Muscle Selectivity in Bradykinin Analogs with Multiple D–Amino Acid Substitutions", Dept. of Biochem., Univ of Colorado School of Medicine, Denver, Colorado.
J. Rifo et al., "Bradykinin Receptor Antagonists Used To Characterize the Heterogeneity of Bradykinin–induced Responses in Rat vas Deferens", European Journal of Pharmacology, 142 (1987), pp. 305–312.
I. J. Zeitlin et al., "Mobilization of Tissue Kallikrein in Inflammatory Disease of the Colon," Wolfson Labs; Gastrointestinal Unit, West, Gen. Hosp. and Dept. of Clinical Surgery, Univ. of Edinburgh (1972), pp. 133–138.
Kenji Suzuki et al, "Synthesis of Every Kinds of Peptide Fragments of Bradykinin" Chemical Pharm. Bull. (1969) vol. 17, pp. 1671–1678.
Zabrocki et al.; J. Org. Chem.; Conformational Mimicry. 3. Synthesis and Incorporation of 1,5–Disubstituted Tetra–zole Dipeptide Analogues into Peptides with Preservation of Chiral Integrity: Bradykinin; vol. 57, No. 1, 1992; pp. 202–209.
Hodges et al.; Peptides Chemistry, Structure and Biology; Proceedings of the Thirteenth American Peptide Symposium Jun. 20–25, 1993; pp. 381–383.

(List continued on next page.)

Primary Examiner—David Lukton
Attorney, Agent, or Firm—Foley & Lardner

[57] ABSTRACT

Novel compounds with as few as three natural amino acids that incorporate a substituted 4-keto-1,3,8-triazaspiro[4.5] decan-3-alkanoyl bridge in place of selected fragments of peptidic bradykinin receptor antagonists are pseudopeptides with potent bradykinin receptor antagonist actions. These pseudopeptides and their pharmaceutical compositions are of benefit in treating conditions and diseases of mammals, including humans, in which an excess of bradykinin or a related kinin is produced endogenously or is received exogenously, for example via insect bite.

7 Claims, No Drawings

OTHER PUBLICATIONS

Kyle et al.; Journal of Medical Chemistry; A proposed Model of Bradykinin Bound to the Rat B2 Receptor and Its Utility for Drug Design; vol. 37, No. 9; 29 Apr. 1994; pp. 1347–1354.

American Chemical Society; Abstracts of Papers; Washington, D.C. Aug. 21–25, 1994.

Kyle; Journal of Medicinal Chemistry; NMR and Computational Evidence that High–Affinity Bradykinin Receptor Antagonists Adopt C–Terminal $\beta$–Turns; vol. 36, No. 10; May 14, 1993, pp. 1450–1460.

Hodges et al.; Peptides Chemistry, Structure and Biology; Proceedings of the Thirteenth American Peptide Symposium Jun. 20–25, 1993; pp. 449–451.

1

BRADYKININ ANTAGONIST PSEUDOPEPTIDE DERIVATIVES OF SUBSTITUTED 4-KETO-1,3,8-TRIAZASPIRO[4.5] DECAN-3-ALKANOIC ACIDS

This application is a continuation application under 37 CFR 1.62 of prior application Ser. No. 08/118,558, filed on Sep. 9, 1993 now abandoned, which is a continuation-in-part of Ser. No. 07/957,879 filed Oct. 8, 1992, now U.S. Pat. No. 5,521,158 entitled, BRADYKININ ANTAGONIST PSEUDOPEPTIDE DERIVATIVES OF SUBSTITUTED 4-KETO-1,3,8-TRIAZASPIRO[4.5]DECAN-3-ALKANOIC ACIDS

FIELD OF THE INVENTION

This invention relates to compounds which are bradykinin receptor antagonists and to pharmaceutical compositions and methods for using these compounds to antagonize the effects of bradykinin in mammals, including humans. More specifically, the invention relates to pseudopeptides which incorporate a substituted 4-keto-1,3,8-triazaspiro[4.5]decan-3-alkanoic acid as a replacement for selected fragments of the amino acid sequence of bradykinin receptor antagonist peptides.

BACKGROUND OF THE INVENTION

Bradykinin is a linear nonapeptide $Arg^1$-$Pro^2$-$Pro^3$-$Gly^4$-$Phe^5$-$Ser^6$-$Pro^7$-$Phe^8$-$Arg^9$ that is produced endogenously in humans and other mammals as a result of the action of kallikreins, a group of proteolytic enzymes present in most tissues and body fluids, on kininogens. Once formed, this neuropeptide apparently plays an important role in inflammatory processes. It produces a number of effects associated with pain and intimation. Observations that the kallikrein-kinin system is activated to overproduce bradykinin in pathological conditions such as septic shock, anaphylaxis, rhinitis, asthma, various forms of arthritis, and inflammatory bowel disease further support the role of this endogenous peptide as a mediator of pain and inflammation. The effects of bradykinin on the cardiovascular and respiratory systems are also notable. It causes vasodilation with a concomitant fall in blood pressure. Accordingly, it has been implicated in the pathogenesis of shock, notably septic and endotoxic shock. The potent bronchoconstriction elicited by bradykinin in animals and humans has resulted in its implication in airway inflammatory conditions such as allergic asthma and rhinitis.

As a result of the implication that increased levels of bradykinin may play a part in a number of pathological conditions, considerable research has been aimed toward the derivation of bradykinin receptor antagonism as potential therapeutic agents. The first antagonists of bradykinin to be discovered were peptide relatives of the natural peptide in which L-$Pro^7$ was replaced by D-Phe [Vavrek, R. J. and Stewart, J. M. *Peptides* (1985), 6, 161–164]. Several members of this series, notably D-Arg[$Hyp^3$, $Thi^{5,8}$, D-$Phe^7$]-bradykinin and Lys—Lys[$Hyp^3$, $Thi^{5,8}$, D-$Phe^7$]-bradykinin have been widely studied [Abe, K., Moriya, H. and Fuji, S., Eds. *Adv. Exp. Med. Biol.* (1989), Plenum Press, New York; Griesbacher, T. and Lembeck, F. *Br. J. Pharmacol.* (1987) 92,333–340; Steranka, L. R. et al. *Proc. Natl. Acad. Sci. USA* (1988), 55, 3245–3249]. Typically, these bradykinin antagonist peptides had Ki values in the range of 20–80 μM in guinea pig ileum [Stewart, J. M. and Vavrek, R. J. In *Bradykinin Antagonists: Basic and Clinical Research* (1991). Burch, R. M., Ed., Marcel Dekker, New York].

Subsequently, several classes of bradykinin antagonist peptides with 600-to 1,000-fold greater potency in the guinea pig ileum preparation were disclosed. One such class consists of the initial type of bradykinin antagonist peptides in which two molecules are dimerized via a bis-succinimidohexane cross-link attached to the amino acid residue in position 6 of each of the monomeric peptides. The peptide derived by cross linking two D-Arg [$Hyp^3$, $Cys^6$, D-$Phe^7$, $Leu^8$]-bradykinin molecules in this manner is 50 to 100 times more potent than the monomer [Cheronis, J. C. et al. *J. Med. Chem.* (1992), 35, 1563–1572]. Another more recently described class of bradykinin antagonist peptides has the general structure $Arg^0$-$Arg^1$-$Pro^2$-$Hyp^3$-$Gly^4$-$W^5$-$Ser^6$-D-$X^7$-$Y^8$-$Arg^9$ wherein W is an aromatic amino acid residue, e.g. Phe or Thi, and residues X and Y in position 7 and 8 are conformationally constrained unnatural amino acids, e.g. D-Tic (D-tetrahydroisoquinolinecarboxyl acid), Oic (octahydroindolecarboxylic acid), and Aoc (2-azabicyclo[3.3.0]octane-3-carboxylic acid). Two compounds in this class have been studied with particular intensity. These are of the indicated general structure in which W=Thi, X=D-Tic and Y=Oic (HOE 140) [Rhaleb, N. E. et al. *Eur. J. Pharmacol.* (1992),210, 115–120]and the one in which W=Thi, X=D-Tic and Y=L-Tic (NPC 16731) [Farmer, S. G. et al. *Br. J. Pharmacol.* (1991) 102,785–787].

A more recent series of bradykinin receptor antagonist peptides is novel in that it lacks the D-aromatic amino acid residue critical to the activity of the earlier described antagonists of the endogenous neuropeptide. In this group of compounds having the general bradykinin antagonist structure W (in position 5) is Phe or Thi, X (in position 8) is Tic or Oic. Two members of this series, namely D-Arg—Agr-Pro-Hyp-Gly-Phe-Ser-D-Hype(trans-SPh)-Oic-Arg (NPC 17661) and the corresponding peptide having D-Hype-(transPr) in position 7 (NPC 17331) have been studied extensively. They are extremely potent bradykinin receptor antagonists [Kyle, D. J. and Burch, R. M. *Curr. Opin. Invest. Drugs* (1993), 2, 5–20].

A limitation of the bradykinin antagonist peptides is their lack of oral activity. Thus, these compounds must be administered parenterally, e.g. by local or topical application, by inhalation or by various routes of systemic injection. Further, peptides in general have a relatively short duration of action as a consequence of their rapid metabolic degradation. As a result, non-peptide or semi-peptide bradykinin receptor antagonists that lack the limitations of a peptide offer meaningful therapeutic advantages. To date, however, potent and selective non-peptide bradyinin receptor antagonists have not been reported. Only functional antagonism, not mediated by receptor binding, has been observed for a miscellaneous group of non-peptides [Calixto, J. B. et al. In *Bradykinin Antagonists: Basic and Clinical Research* (1991), Burch, R. M., Ed., Marcel Dekker, New York; Burch, R. M., Farmer, S. G. and Steranka, L. R. *Med. Res. Rev.* (1990), 10 237–269].

SUMMARY OF THE INVENTION

The present invention resides in the discovery that novel pseudopeptides that incorporate a 4-keto-1,3,8-triazaspiro [4.5]decan-3-alkanoyl group as indicated in the general structure of formula 1 illustrated below are effective bradykinin receptor antagonism. The compounds are useful in the treatment of various pathophysiological disorders including burn pain and inflammatory diseases such as arthritis, asthma and septic shock.

Another embodiment of the invention involves a pharmaceutical composition useful as a bradykinin receptor antagonist that is comprised of an effective amount of the novel pseudopeptide derivative of a substituted 4-keto-1,3,8-triazaspiro[4.5]decan-3-alkanoic acid in a suitable pharmaceutical carrier. The invention also involves a process for blocking bradykinin receptor activation in mammals which comprises administering to a subject an amount of the novel compound to effectively antagonize the adverse pathophysiological effects resulting from the neuropeptide-receptor interaction.

A further embodiment involves a pharmaceutical preparation for treating local pain and inflammation from burns, wounds, cuts, rashes and other such trauma, and pathological responses caused by the production of bradykinin or related kinins by an animal which entails administering an amount of the novel pseudopeptide in a suitable pharmaceutical carrier to effectively block the reactions to bradykinin. Another aspect of this invention involves a process for treating local pain and inflammation which comprises administering an effective amount of the pharmaceutical preparation to an animal in need thereof.

DETAILED DESCRIPTION OF THE INVENTION

The presently invented compounds which are bradykinin receptor antagonists have the following formula (1):

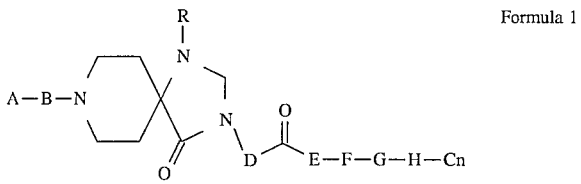

Formula 1 wherein
A is hydrogen or is selected from the group consisting of the L-and D-isomers of Arg, Gln, Asn, Lys, Sar, N-ε-acetyl-Lys, $N^G$-p-tosyl-Arg, $N^G$-nitro-Arg, Lys—Lys, acetyl-Arg, and citrulline;
B is a direct bond or is selected from the group consisting of the L-and D-isomers of Arg, Gln, Asn, Lys, Sar, N-ε-acetyl-Lys, $N^G$-p-tosyl-Arg, $N^G$-nitro-Arg, acetyl-Arg, and citrulline;
R is selected from the group consisting of a substituted or unsubstituted aryl group, a straight, branched, saturated or unsaturated lower alkyl chain of 1 to 6 carbon atoms, and a cycloalkyl or cycloalkylmethyl moiety in which the cycloalkyl ring comprises 3 to 6 carbon atoms;
D is a saturated or unsaturated alkylene bridge consisting of 1 to 8 carbon atoms optionally substituted with a benzyl or naphthyl group or in which one of the carbon atoms of the bridge is disubstituted to form a cycloalkyl ring consisting of 3 to 6 carbon atoms;
E is a direct bond or selected from the group consisting of Ser, Thr, Gly, N-BnGly, Val, Ala, Cys and Tyr,
F is selected from the group consising of a D-aromatic amino acid and a D-Hype;
G is selected from the group consisting of Oic, Aoc, Thz, octahydro-1H-isoindole-1-carboxylic acid, pipecolinic acid, Pro, 4Hyp, azetidine-2-carboxylic acid, Aib, Leu, Ile, Vat, Phe, Thi, Tic, indoline-2-carboxylic acid, homoPhe, Trp, Tyr, Nal, and a Hype;
H is selected from the group consisting of Arg, Orn, Asn, Gln, and Lys;
Cn is a hydroxyl group or a C-terminal extension selected from the group consisting of carboxamido, alkoxy, an acidic, basic or neutral aliphatic, aromatic, or cylic amino acid residue of the D-or L-configuration;
and pharmaceutically accepted salts thereof.

In a particularly preferred embodiment, the aryl group of R is selected from the group consisting of a phenyl, naphthyl, benzyl or naphthylmethyl group optionally substituted with a $C_1$ to $C_4$ lower alkyl group, a $C_1$ to $C_4$ alkoxyl group or a halogen.

A particularly preferred pseudopeptide includes those wherein:
A is D-Arg;
B is Arg;
R is selected from the group consisting of a substituted or unsubstituted aryl group, a straight, branched, saturated or unsaturated lower alkyl chain of 1 to 6 carbon atoms, and a cycloalkyl or cycloalkylmethyl moiety in which the cycloalkyl ring comprises 3 to 6 carbon atoms;
D is a saturated or unsaturated alkylene bridging group consisting of 1 to 8 carbon atoms optionally substituted with a benzyl or naphthyl group;
E is a direct bond or is selected from the group consisting of Ser, Gly, N-BnGly, and Ala;
F is selected from the group consising of a D-Phe, D-Tic and a D-Hype;
G is selected from the group consisting of Oic, Aoc, Phe, and a Hype;
H is Arg;
Cn is selected from the group consisting of a hydroxyl group, a carboxamido group, and an alkoxy group.

Another preferred embodiment includes a pseudopeptide wherein:
A is D-Arg;
B is Arg;
R is selected from the group consisting of phenyl, 4-methylphenyl, 4-methoxyphenyl, 4-fluorophenyl, 4-chlorophenyl, benzyl, 1-naphthyl, 2-naphthyl, cyclohexyl, cyclohexylmethyl, n-propyl, n-pentyl, and neopentyl;
D is a saturated or unsaturated alkylene bridging group consisting of 1 to 4 carbon atoms;
E is a direct bond or Ser;
F is selected from the group consisting of D-Phe, D-Tic and a D-Hype;
G is Oic;
H is Arg; and
Cn is OH.

Most preferred is a pseudopeptide wherein:
A is D-Arg;
B is Arg;
R is selected from the group consisting of phenyl, 4-methylphenyl, cyclohexyl, cyclohexylmethyl and n-propyl;
D is $CH_2$ or when E is a direct bond $(CH_2)_4$;
E is selected from the group consisting of a direct bond, Ser, N-BnGly, Gly, and Ala;
F is selected from the group consisting of D-Phe, D-Tic and a D-Hype;
G is Oic;
H is Arg; and
Cn is a hydroxyl group.

Other preferred pseudopeptides of the invention include but are not limited to the following compounds wherein X signifies the group:

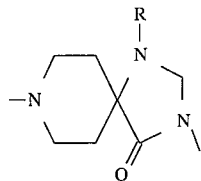

in which the substituent R is described in brackets [R]:
H-D-Arg—Agr-X[Ph]-CH₂CO-Ser-D-Tic-Oic-Arg-OH
H-D-Arg—Agr-X[4-CH₃Ph]-CH₂CO-Ser-D-Tic-Oic-Arg-OH
H-D-Arg—Agr-X[4-CH₃OPh]-CH₂CO-Ser-D-Tic-Oic-Arg-OH
H-D-Arg—Agr-X[4-FPh]-CH₂CO-Ser-D-Tic-Oic-Arg-OH
H-D-Arg—Agr-X[4-ClPh]-CH₂CO-Ser-D-Tic-Oic-Arg-OH
H-D-Arg—Agr-X[1-naphthyl]-CH₂CO-Ser-D-Tic-Oic-Arg-OH
H-D-Arg—Agr-X[2-naphthyl]-CH₂CO-Ser-D-Tic-Oic-Arg-OH
H-D-Arg—Agr-X[Bn]-CH₂CO-Ser-D-Tic-Oic-Arg-OH
H-D-Arg—Agr-X[(CH₂)₄CH₃]-CH₂CO-Ser-D-Tic-Oic-Arg-OH
H-D-Arg—Agr-X[(CH₂)₄CH₃]-CH₂CO-Ser-D-Tic-Oic-Arg-OH
H-D-Arg—Agr-X[CH₂C(CH₃)₃]-CH₂CO-Ser-D-Tic-Oic-Arg-OH
H-D-Arg—Agr-X[c-C₆H₁₁]-CH₂CO-Ser-D-Tic-Oic-Arg-OH
H-D-Arg—Agr-X[c-C₆H₁₁CH₂]-CH₂CO-Ser-D-Tic-Oic-Arg-OH
H-D-Arg—Agr-X[Ph]-CH₂CO-Ser-D-Hype(trans SPh)-Oic-Arg-OH
H-D-Arg—Agr-X[4-CH₃Ph]-CH₂CO-Ser-D-Hype(trans SPh)-Oic-Arg-OH
H-D-Arg—Agr-X[4-CH₃OPh]-CH₂CO-Ser-D-Hype(trans SPh)-Oic-Arg-OH
H-D-Arg—Agr-X[4-FPh]-CH₂CO-Ser-D-Hype(trans SPh)-Oic-Arg-OH
H-D-Arg—Agr-X[4-ClPh]-CH₂CO-Ser-D-Hype(trans SPh)-Oic-Arg-OH
H-D-Arg—Agr-X[1-naphthyl]-CH₂CO-Ser-D-Hype(trans SPh)-Oic-Arg-OH
H-D-Arg—Agr-X[2-naphthyl]-CH₂CO-Ser-D-Hype(trans SPh)-Oic-Arg-OH
H-D-Arg—Agr-X[Bn]-CH₂CO-Ser-D-Hype(trans SPh)-Oic-Arg-OH
H-D-Arg—Agr-X[(CH₂)CH₃]-CH₂CO-Ser-D-Hype(trans SPh)-Oic-Arg-OH
H-D-Arg—Agr-X[(CH₂)₄CH₃]-CH₂CO-Ser-D-Hype(trans SPh)-Oic-Arg-OH
H-D-Arg—Agr-X[CH₂C(CH₃)₃]-CH₂CO-Ser-D-Hype(trans SPh)-Oic-Arg-OH
H-D-Arg—Agr-X[c-C₆H₁₁]-CH₂CO-Ser-D-Hype(trans SPh)-Oic-Arg-OH
H-D-Arg—Agr-X[c-C₆H₁₁CH₂]-CH₂CO-Ser-D-Hype(trans SPh)-Oic-Arg-OH
H-D-Arg—Agr-X[Ph]-CH₂CO-Ser-D-Hype(trans n-Pr)-Oic-Arg-OH
H-D-Arg—Agr-X[4-CH₃Ph]-CH₂CO-Ser-D-Hype(trans n-Pr)-Oic-Arg-OH
H-D-Arg—Agr-X[4-CH₃OPh]-CH₂CO-Ser-D-Hype(trans n-Pr)-Oic-Arg-OH
H-D-Arg—Agr-X[4-FPh]-CH₂CO-Ser-D-Hype(trans n-Pr)-Oic-Arg-OH
H-D-Arg—Agr-X[4-ClPh]-CH₂CO-Ser-D-Hype(trans n-Pr)-Oic-Arg-OH
H-D-Arg—Agr-X[1-naphthyl]-CH₂CO-Ser-D-Hype(trans n-Pr)-Oic-Arg-OH
H-D-Arg—Agr-X[2-naphthyl]-CH₂CO-Ser-D-Hype(trans n-Pr)-Oic-Arg-OH
H-D-Arg—Agr-X[Bn]-CH₂CO-Ser-D-Hype(trans n-Pr)-Oic-Arg-OH
H-D-Arg—Agr-X[(CH₂)₂CH₃]-CH₂CO-Ser-D-Hype(trans n-Pr)-Oic-Arg-OH
H-D-Arg—Agr-X[CH₂C( CH₃)₃]-CH₂CO-Ser-D-Hype(trans n-Pr)-Oic-Arg-OH
H-D-Arg—Agr-X[c-C₆H₁₁]-CH₂CO-Ser-D-Hype(trans n-Pr)-Oic-Arg-OH
H-D-Arg—Agr-X[c-C₆H₁₁CH₂]-CH₂CO-Ser-D-Hype(trans n-Pr)-Oic-Arg-OH
H-D-Arg—Agr-X[Ph]-CH₂CO-N-BnGly-D-Tic-Oic-Arg-OH
H-D-Arg—Agr-X[Ph]-CH₂CO-N-BnGly-D-Hype(trans SPh)-Oic-Arg-OH
H-D-Arg—Agr-X[Ph]-CH₂CO-N-BnGly-D-Hype(trans n-Pr)-Oic-Arg-OH
H-D-Arg—Agr-X[c-C₆H₁₁CH₂]-CH₂CO-N-BnGly-D-Tic-Oic-Arg-OH
H-D-Arg—Agr-X[c-C₆H₁₁CH₂]-CH₂CO-N-BnGly-D-Hype(trans SPh)-Oic-Arg-OH
H-D-Arg—Agr-X[c-C₆H₁₁CH₂]-CH₂CO-N-BnGly-D-Hype(trans n-Pr)-Oic-Arg-OH
H-D-Arg—Agr-X[Ph]-(CH₂)₄CO-D-Tic-Oic-Arg-OH
H-D-Arg—Agr-X[Ph]-(CH₂)₄CO-D-Hype(trans SPh)-Oic-Arg-OH
H-D-Arg—Agr-X[Ph]-(CH₂)₄CO-D-Hype(trans n-Pr)-Oic-Arg-OH
H-D-Arg—Agr-X[c-C₆H₁₁CH₂]-(CH₂)₄CO-D-Tic-Oic-Arg-OH
H-D-Arg—Agr-X[c-C₆H₁₁CH₂]-( CH₂)₄CO-D-Hype(trans SPh )-Oic-Arg-OH
H-D-Arg—Agr-X[c-C₆H₁₁CH₂]-(CH₂)₄CO-D-Hype(trans n-Pr)-Oic-Arg-OH
H-D-Arg—Agr-X[Ph]-CH₂CH=CH-CH₂CO-D-Tic-Oic-Arg-OH
H-D-Arg—Agr-X[Ph]-CH₂CH=CH-CH₂CO-D-Hype(trans SPh)-Oic-Arg-OH
H-D-Arg—Agr-X[Ph]-CH₂CH=CH-CH₂CO-D-Hype(trans n-Pr)-Oic-Arg-OH
H-D-Arg—Agr-X[c-C₆H₁₁CH₂]-CH₂CH=CH CH₂CO-D-Tic-Oic-Arg-OH
H-D-Arg—Agr-X[c-C₆H₁₁CH₂]-CH₂CH=CH CH₂CO-D-Hype(trans SPh)-Oic-Arg-OH
H-D-Arg—Agr-X[c-C₆H₁₁CH₂]-CH₂CH=CH CH₂CO-D-Hype(trans n-Pr)-Oic-Arg-OH
H-D-Arg—Agr-X[Ph]-CH₂CH₂C[(CH₂)₂]CH₂CO-D-Tic-Oic-Arg-OH
H-D-Arg—Agr-X[Ph]-CH₂CH₂C[(CH₂)₂]CH₂CO-D-Hype(trans SPh)-Oic-Arg-OH
H-D-Arg—Agr-X[Ph]-CH₂CH₂C[(CH₂)₂]CH₂CO-D-Hype(trans n-Pr)-Oic-Arg-OH
H-D-Arg—Agr-X[Ph]-CH₂CO-Ala-D-Tic-Oic-Arg-OH
H-D-Arg—Agr-X[Ph]-CH₂CO-Ala-D-Hype(trans SPh)-Oic-Arg-OH
H-D-Arg—Agr-X[Ph]-CH₂CO-Ala-D-Hype(trans n-Pr)-Oic-Arg-OH
H-D-Arg—Agr-X[c-C₆H₁₁CH₂]-CH₂CO-Ala-D-Tic-Oic-Arg-OH
H-D-Arg—Agr-X[c-C₆H₁₁CH₂]-CH₂CO-Ala-D-Hype(trans SPh)-Oic-Arg-OH H-D-Arg—Agr-X[c-C$_6$H$_{11}$CH$_2$]-CH$_2$CO-Ala-D-Hypc-(trans n-Pr)-Oic-Arg-OH
H-D-Arg—Agr-X[Ph]-CH$_2$CO-Gly-D-Tic-Oic-Arg-OH
H-D-Arg—Agr-X[Ph]-CH$_2$CO-Gly-D-Hypc(trans SPh)-Oic-Arg-OH
H-D-Arg—Agr-X[Ph]-CH$_2$CO-Gly-D-Hypc(trans n-Pr)-Oic-Arg-OH
H-D-Arg—Agr-X[c-C$_6$H$_{11}$CH$_2$]-CH$_2$CO-Gly-D-Tic-Oic-Arg-OH
H-D-Arg—Agr-X[c-C$_6$H$_{11}$CH$_2$]-CH$_2$CO-Gly-D-Hypc-(trans SPh)-Oic-Arg-OH
H-D-Arg—Agr-X[c-C$_6$H$_{11}$CH$_2$]-CH$_2$CO-Gly-D-Hypc-(trans n-Pr)-Oic-Arg-OH As used in the specification and claims, "alkyl" is a paraffinic hydrocarbon group which may be derived from an alkane by dropping one hydrogen from the formula, such as methyl, ethyl, propyl, isopropyl, butyl, and so forth; "substituted C$_1$–C$_6$ alkyl" is a branched alkyl, such as methylbutyl; "aryl" is an aromatic ring compound such as phenyl (Ph), naphthyl; "substituted aryl" is a substituted aromatic ring, such as phenyl with alkyl, alkoxy, or halogen substitution; and "aralkyl" is a aryl being attached through an alkyl chain, straight or branched, containing from one through six carbons, such as benzyl (Bn) or phenylpropyl group. A "direct bond" is a bond which replaces a particular amino acid compound between adjacent amino acids and which ammo acid may also be indicated to be absent by the term "null". The phrase "a suitable amine protecting group" is a group, such as Boc (tert-butyloxycarbonyl) protecting group, which protects the amine moiety from reaction and which can be removed under mild conditions so as not to affect the rest of the molecule.

Definitions of the amino acid abbreviations used herein are as follows:

Arg is arginine; Ala is alanine; Aib is 2-aminoisobytyric acid; Aoc is (S,S,S)-2-azabicyclo [3.3.0]octane-3-carboxylic acid; Asn is asparagine; Asp is aspartic acid; Cys is cysteine; Gln is glutamine; Glu is glutamic acid; Gly is glycine; N-BnGly is N-benzylglycine; Ile is isoleucine; Leu is leucine; Lys is lysine; Mct is methionine; Nal is beta-2-naphthylalanine; Orn is ornithine; Pro is proline; homoPhe is homophenylalanine; 4Hyp is 4-hydroxyproline; Ser is serine; Sar is sarcosine; Thi is beta-2-thienylalanine; Thr is threonine; Thz is thiazolidine-4-carboxylic acid; Phe is phenylalanine; Tic is 1,2,3,4-tetrahydroisquinoline-3-carboxylic; Oic is (2S, 3aS, 7aS)-octahydro-1H-indole-2-carboxylic acid; Val is valine; D-Hype (trans n-Pr) is 4S-D-prolyl propyl ether and represents:

"Hype" is defined herein as having the following structure:

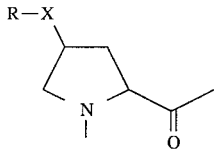

wherein R is selected from the group consisting of H, C$_1$–C$_6$ alkyl, substituted C$_1$–C$_6$ alkyl, C$_2$–C$_8$ alkenyl, C$_2$–C$_8$ cycloalkyl, C$_3$–C$_8$ cycloalkyl substituted C$_1$–C$_6$ alkyl, an aryl group, a substituted aryl group wherein the substituent is C$_1$–C$_4$ alkyl, C$_1$–C$_4$ alkoxy, halogen or trifluoromethyl, an arylalkyl group, and a group of the formula R$^1$NHC(O)-where R$^1$ is C$_1$–C$_6$ alkyl or aryl, and where X is either SO$_n$ or oxygen, and n=0, 1, or 2;

D-Hype (trans-propyl) is 4S-D-prolyl propyl ether and represents

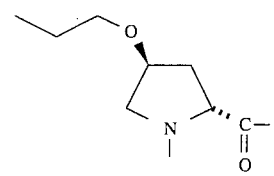

D-Hype (trans-thiophenyl) or D-Hype(trans-SPh) is 4S-D-prolyl phenyl thioether, also known as
D-4-hydroxyproline trans phenylthioether also known as D-Hyp S(trans-phenyl) and represents

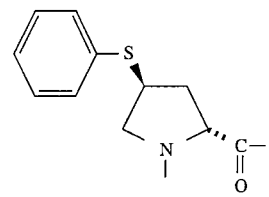

D-Hypc (trans-phenylpropyl) represents

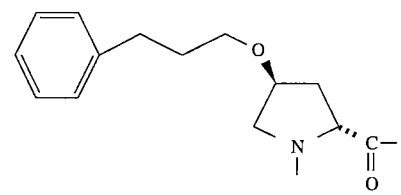

D-Hype (trans-2-methylbutyl) represents

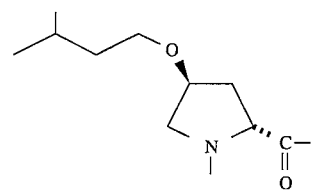

D-Hype (trans-ethyl) represents

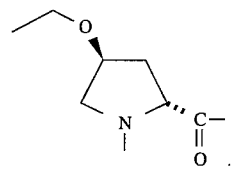

D-Hype (trans-methyl) represents

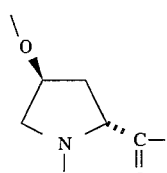

All amino acids residues, except Sar and Gly, described in the specification are preferably the L-configuration unless otherwise specified. It would be recognized, however, that the 7 position must always be the D-configuration whereas the hydroxyproline ethers and thioethers of position 8 may be either in the D- or L- configuration. The hydroxyproline ethers at position 7 are preferably in a trans configuration, whereas the hydroxyproline ethers at position 8 can be in either the cis or trans configuration. The symbols and abbreviations used for amino acids, their derivatives and protecting groups, and peptides and their salts are those customarily used in peptide chemistry. [(See *Biochem. J.* (1972), 126, 773), which Journal reference is hereby incorporated by reference.]

The synthesis of the peptides of this invention including derivation, activation, and coupling of protected amino acid residues, and their purification, and the analytical methods for determining identity and purity are included in the general body of knowledge of peptide chemistry, as described in Houben Weyl *Methoden der Organischen Chemie*, (1974), Vol. 16, pans I & II for solution-phase synthesis, and in *Solid Phase Peptide Synthesis*, (1984), by Stewart and Young for synthesis by the solid-phase method of Merrifield can be performed by any chemist skilled in the an of peptide synthesis by standard solution methods or by manual or automated solid phase methods.

Aoc can be prepared by the method of V. Teetz, R. Geiger and H. Gaul, *Tetrahedron Lett.* (1984), 4479. Tic can be prepared by the method of K. Hayashi, Y. Ozaki, K. Nunami and N. Yoneda, *Chem. Pharm. Bull.* (1983) 31,312.

The appropriate hydroxyproline substituents used at position 7 or 8 are prepared by the process described in PCT publications WO 92/18155 and WO 92/18156 which are herein incorporated by reference. The starting materials are commercially available and can be prepared by known procedures. Both the cis and trans stereoisomers can be prepared by these means and are within the scope of the present invention.

Also included in the scope of this invention are compounds as described above having the following formula, wherein X=0, 1 or 2.

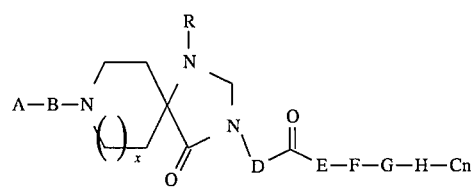

Formula 2

Substituted 4-keto-1,3,8-triazaspiro[4.5]decan-3-alkanoic acids suitably protected for incorporation into a pseudopeptide are prepared by the general sequence outlined in Scheme I which is modeled after a previously described procedure [Janssen, P.A.J., U.S. Pat. No. 3,155,670, Nov. 3, 1964; U.S. Pat. No. 3,155,669, Nov. 3, 1964; Scharpf, W. G., U.S. Pat. No. 3,839,342, Oct. 1, 1974]

Scheme I

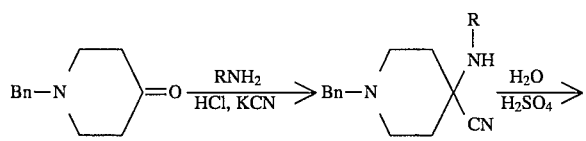

Scheme I

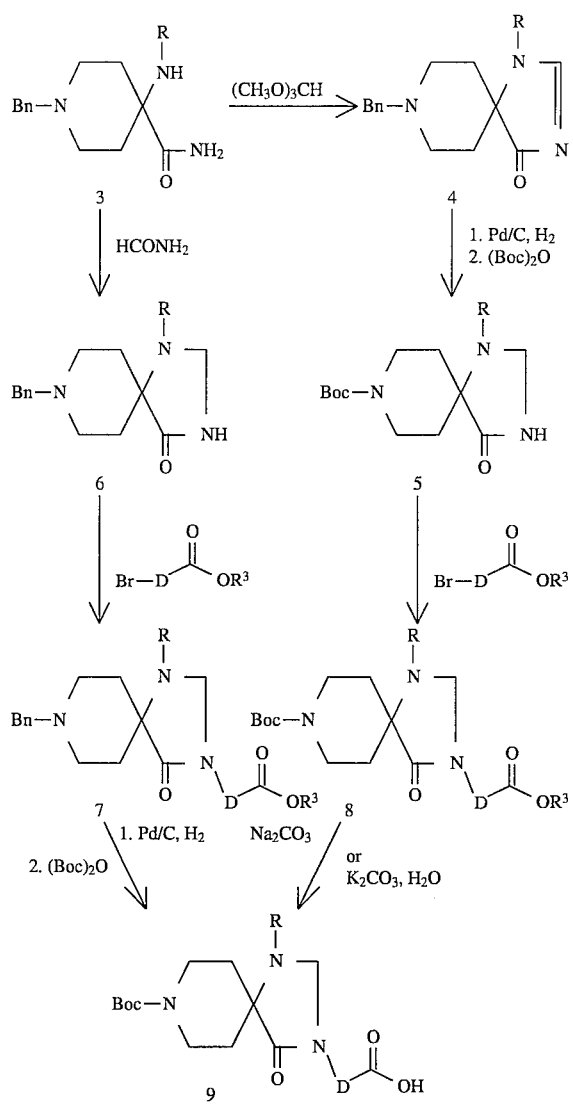

where: R and D are as defined for formula 1; $R^3$ is $CH_3$, $C_2H_5$ or Bn.

Accordingly, N-benzylpiperidone (1) was treated with cyanide and the appropriate amine ($RNH_2$) to produce the corresponding 4-amino-4-cyanopiperidine (2) which was hydrolyzed to the carboxamide (isonipecotamide, 3). Condensation of 3 with trimethoxymethane (methyl orthoformate) afforded the 1-substituted 8-benzyl-1,3,8-triazaspiro [4.5]dec-2-en-4-one (4) whereas similar condensation with formamide gave the 1-substituted 8-benzyl-1,3,8-triazaspiro [4.5]decan-4-one (5). Conversion of 4 to a Boc-protected 1-substituted 4-keto-1,3,8-triazaspiro[4.5]decan-3-alkanoic acid 8 proceeded via 5. Thus, catalytic hydrogenolysis of the benzyl substitutent of 4 followed by Boc protection with di-tert-butyl dicarbonate produced 5. Alkylation of 5 with the appropriate alkyl bromalkanoate afforded the ester 8 which upon ester hydrolysis gave 9. Alternatively, synthesis of 9 from 6 proceeded by alkylation with the requisite benzyl bromoalkanoate to afford 7 which was catalytically hydrogenolyzed and then Boc-protected as indicated in Scheme I.

In some instances, previously described or commercially available intermediates were employed in the sequence. Thus, 1-phenyl-1,3,8-triazaspiro[4.5]decan-4-one was treated with di-tert-butyl dicarbonate to give 5 (R=Ph). 1-Benzyl-4-(p-toluidino)isonipecotamide (3, R=4-CH₃Ph) and 1-benzyl-4-(n-propylamino)-4-carboxamide (3, R=n-Pr) were obtained from commercial sources.

The preparation of compounds for administration in pharmaceutical preparations may be performed by a variety of methods well known to those skilled in the art. Appropriate pharmaceutically acceptable salts within the scope of the invention are those derived from mineral acids such as hydrochloric acid, hydrobromic acid, phosphoric acid, nitric acid, and sulfuric acid; and organic acids such as tartaric acid, fumaric acid, lactic acid, oxalic acid, ethanesulfonic acid, p-toluenesulfonic acid, and the like, giving the hydrochloride, hydrobromide, phosphate, nitrate, sulfate, tartrate, fumarate, lactate, oxalate, ethanesulfonate, p-toluensulfonate, and the like, salt, respectively.

ADMINISTRATION AND USE

Therapeutic applications of the novel bradykinin antagonism include not only treatment for the production of bradykinin or related kinins by the animal but also the injection of bradykinin related peptides into an animal as a result of bites and stings. Topical application alone or in combination with subcutaneous utilization of the bradykinin antagonists of the invention can be employed to treat the effects of bradykinin-related peptides causing pain, inflammation and swelling.

The therapeutic use of bradykinin antagonists of this invention for other traumatic inflammatory or pathological conditions which are known to be mediated by bradykinin or exacerbated by an overproduction of bradykinin can also be achieved. These conditions include local trauma such as wounds, burns, rashes, angina, arthritis, asthma, allergies, rhinitis, shock, inflammatory bowel disease, low blood pressure, and systemic treatment of pain and inflammation.

In parenteral administration of the novel compounds and compositions of the invention the compounds may be formulated in aqueous injection solutions which may contain antioxidants, buffers, bacteriostats, etc. Extemporaneous injection solutions may be prepared from sterile pills, granules, or tablets which may contain diluents, dispersing and surface active agents, binders and lubricants which materials are well known to the ordinary skilled artisan.

In the case of oral administration, fine powders or granules of the compound may be formulated with diluents and dispersing and surface active agents, and may be prepared in water or in a syrup, in capsules or cashets in the dry state or in a non-aqueous suspension, where a suspending agent may be included. The compounds may also be administered in tablet form along with optional binders and lubricants, or in a suspension in water or syrup or an oil or in a water/oil emulsion and may include flavoring, preserving, suspending, thickening, and emulsifying agents. The granules or tablets for oral administration may be coated. Other pharmaceutically acceptable agents and formulations which are well known to those skilled in the pharmaceutical art may be utilized.

Solid or liquid careers can also be used. Solid careers include starch, lactose, calcium sulfate dihydrate, terra alba, sucrose, talc, gelatin, agar, pectin, acacia, magnesium stearate, and stearic acid. Liquid careers include syrup, peanut oil, olive oil, saline, and water. Ointments and creams are prepared using various well known hydrophilic and hydrophobic bases. Topical reservoirs are suitably prepared using known polymeric materials such as various acrylic-based polymers selected to provide desired release characteristics. Suppositories are prepared from standard vehicles such as polyethylene glycol and cocoa butter.

The method of treatment according to this invention comprises administering internally or topically to a subject an effective amount of the active compound. Doses of active compounds in the inventive method and pharmaceutical compositions containing same are an efficacious, nontoxic quantity selected from the range of 0.01 to 500 mg/kg of active compound, preferably 0.1 to 50 mg/kg. Persons skilled in the an using routine clinical testing are able to determine optimum doses for the particular ailment being treated. The desired dose is administered to a subject from 1 to 6 or more times daily, intraveneously, orally, rectally, parenterally, topically, or by inhalation.

The efficacy of the inventive compounds of this invention as bradykinin receptor antagonists can be determined using the bradykinin binding and tissue assays described herein. The results of these assays demonstrate that the novel cyclic compounds are potent, selective bradykinin receptor antagonists.

The following examples are illustrative of preferred embodiments of methods of preparation and compounds of the invention and are not to be construed as limiting the invention thereto.

EXAMPLES

The synthesis of the pseudopeptides of this invention including derivation, activation, and coupling of protected amino acid residues, and their purification, and the analytical methods for determining identity and purity are included in the general body of knowledge of peptide chemistry, as described in Houben Weyl *Methoden der Organischen Chemie*, (1974), Vol. 16, parts I & II for solution-phase synthesis, and in *Solid Phase Peptide Synthesis*, (1984), by Stewart and Young for synthesis by the solid phase method of Merrifield.

Any chemist skilled in the an of peptide synthesis can synthesize the peptides of this invention by standard solution methods or by manual or automated solid phase methods.

Example 1

Synthesis of 8-(t-Butoxycarbonyl)-4-keto-1-phenyl-1,3,8-triazaspiro[4.5]decan-3-acetic Acid (9, R=Ph, D=CH₂)

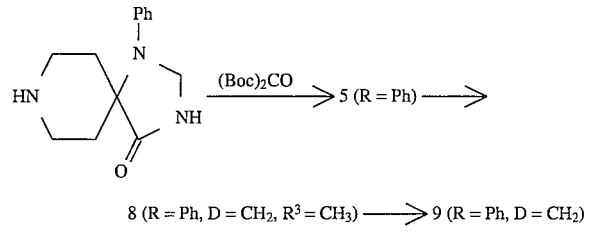

8 (R = Ph, D = CH₂, R³ = CH₃) ⟶ 9 (R = Ph, D = CH₂)

1. Preparation of 8-(t-Butoxycarbonyl)-1-phenyl-1,3,8-triazaspiro[4.5]decan-4-one (5, R=Ph).

A mixture of 3.31 g (10 mmol) of 1-phenyl-1,3,8-triazaspiro[4.5]decan-4-one (Aldrich Chem. Co., Inc., Milwaukee, Wis. di-tert-butyl dicarbonate (7.93 g, 36.3 mmol) and sodium carbonate (4.4 g, 41.5 mmol) in 300 ml of isopropanol and 100 ml of water was stirred at ambient temperature for 24 hours. After the mixture was concentrated to 100 ml in vacuo, it was extracted with ethyl acetate. The organic extracts were washed with water and dried over anhydrous sodium sulfate. After the solution was concentrated, the solid residue was recrystallized from ethanol to give 7.92 g (69.1%) of colorless crystals, mp 216°–217° C., of $\underline{5}$ (R=Ph).

2. Preparation of Methyl 8-(t-Butoxycarbonyl)-4-keto-1-phenyl-1,3,8-triazaspiro[4.5]decan-3-acetate($\underline{8}$, R=Ph, D=CH$_2$).

To a stirred solution of 2.96 g (7.8 mmol) of 8-(tert-butoxycarbonyl)-1-phenyl-1,3,8-triazaspiro[4.5]decan-4-one in 30 ml of dry dimethylformamide at 0° C. was added, in portions, 0.36 g (12 mmol) of sodium hydride (80% in mineral oil). After the mixture was stirred under argon at 0° C. for 30 minutes, 1.84 g (12 mmol) of methyl bromoacetate was added dropwise. The mixture was stirred as it was allowed to attain ambient temperature and then stirring was continued for 4 hours. The reaction was quenched by addition of a saturated aqueous solution of ammonium chloride. The mixture was extracted with ethyl acetate. The extracts were dried over sodium sulfate, concentrated and chromatographed (ethyl acetate-hexane, 0 to 50% gradient) to afford 3.52 g (87%) of the product as a colorless liquid.

3. Preparation of 8-(t-Butoxycarbonyl)-4-keto-1-phenyl-1,3,8-triazaspiro[4.5]decan-3-acetic acid ($\underline{9}$,R=Ph, D=CH$_2$).

A stirred mixture of 2.96 g (7.8 mmol) of methyl 8-(t-butoxycarbonyl)-4-keto-1-phenyl-1.3.8-triazaspiro[4.5]decan-3-acetate, 2.03 g (14.7 mmol) of potassium carbonate, 30 ml of methanol and 10 ml of water was heated under reflux for 2 hours. The mixture was concentrated to about one-third of its original volume, diluted with 20 ml of water and acidified with 2N HCl at 0° C. The mixture was extracted with ethyl acetate and the extracts were washed with water and brine, dried, and concentrated in vacuo. Recrystallization of the residual solid from ethanol afforded 2.47 g (86%) of colorless crystals, mp 200°–201° C.

Example 2

Synthesis of 5-[8-(t-Butoxycarbonyl)-4-keto-1-phenyl-1,3,8-triazaspiro[4.5]decan-3-yl]pentanoic Acid [9. R=Ph. D=(CH$_2$)$_4$]

$\underline{5}$(R=Ph)→$\underline{8}$[(R=Ph, B=(CH$_2$)$_4$, R$^3$=C$_2$H$_5$]→$\underline{9}$[R=Ph, D=CH$_2$)$_4$]

1. Preparation of Ethyl 5-[8-(t-Butoxycarbonyl)-4-keto-1-phenyl-1,3,8-triazaspiro[4.5]decan-3-yl]pentanoate[8, R=Ph, D=(CH$_2$)$_4$, R$_3$=C$_2$H$_5$]

To a stirred solution of 2.3 g (6.95 mmol) of 8-(t-butoxycarbonyl)-1-phenyl-1,3,8-triazaspiro[4.5]decan-4-one in 40 ml of dry dimethylformamide at 0° C. was added 0.4 g (13 mmol) of sodium hydride (80% in mineral oil). The mixture was stirred at 0° C. under argon for 30 minutes and then ethyl 5-bromopentanoate (2.09 g, 10 mmol) was added dropwise. After being allowed to come to ambient temperature, the mixture was stirred for an additional 20 hours. The mixture was quenched with aqueous ammonium chloride, diluted with water and extracted with ethyl acetate. The extracts were washed with water, dried over magnesium surf ate and concentrated. The residue was purified by column chromatography (silica gel, 0–25% gradient of ethyl acetate in hexane) to provide 2.4 g (75.2%) of the indicated ester as a colorless liquid.

2. Preparation of 5-[8-(t-Butoxycarbonyl)-4-keto-1-phenyl-1,3,8-triazaspiro[4.5]decan-3-yl]pentanoic Acid.

A stirred solution of 2.4 g (5.23 mmol) of ethyl 5-[8-(t-butoxycarbonyl)-4-keto-1-phenyl-1,3,8-triazapiro[4.5]decan-3-yl]pentanoate in 100 ml of methanol and 2.5 g (24 mmol) of sodium carbonate in 50 ml of water was refluxed for 4 hours. The solution was cocentrated to about one-third of its original volume, diluted with water and carefully acidified with 2N HCl. Precipitated product was filtered, dried and recrystallized from ethanol to give 1.8 g (80%) of colorless crystals, mp 167°–168° C.

Example 3

Synthesis of 8-(t-Butoxycarbonyl)-1-cyclohexylmethyl-4-keto-1,3,8-triazaspiro[4,5]decan-3-acetic Acid (9. R=c-C$_6$H$_{11}$CH$_2$, D=CH$_2$)

$\underline{1}$→$\underline{2}$(R=c-C$_6$H$_{11}$CH$_2$)→$\underline{3}$(R=c-C$_6$H$_{11}$CH$_2$)→$\underline{4}$(R=c-C$_6$H$_{11}$CH$_2$)

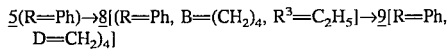

1. Preparation of 1-Benzyl-4-cyano-4-(cyclohexylmethylamino)piperidine ($\underline{2}$, R=c-C$_6$H$_{11}$CH$_2$)

Concentrated hydrochloric acid (10 ml) was added dropwise at 0° C. to a stirred solution of 18.9 g (0.1 mol) of cyclohexylmethylamine in 200 ml of ethanol. To the resulting mixture a solution of 9.75 g (0.15 tool) of potassium cyanide in 25 ml of water was added dropwise with stirring at 0° C. After being stirred at ambient temperature for 3 days, the mixture was concentrated to remove most of the ethanol solvent, diluted with water, and extracted with chloroform. After the extracts were dried over magnesium suflate, they were concentrated. Recrystallization of the residue from isopropyl ether gave 25 g (80.4%) of colorless crystals, mp 128°–130° C.

2. Preparation of 1-Benzyl-4-(cyclohexylmethylamino)piperidine-4-carboxamide ($\underline{3}$, R=c-C$_6$H$_{11}$CH$_2$).

1-Benzyl-4-cyano-4-(cyclohexylmethylaminio)piperidine (10 g, 32.1 mmol) was added in portions, with stirring, to 55 ml of 90% sulfuric acid. After being stirred for an additional 1.5 hours, the mixture was poured into an excess of concentrated aqueous ammonia and ice. The mixture was extracted with chloroform, and the extracts were dried (MgSO$_4$) and concentrated. Recrystallization of the residue from ethyl acetate gave 8.23 g (77.8%) of crystalline product, mp 129°–130° C.

3. Preparation of 8-Benzyl-1-cyclohexylmethyl-1,3,8-triazaspiro[4.5]dec-2-ene-4-one ($\underline{4}$, R=c-C$_6$H$_{11}$CH$_2$)

A stirred mixture of 1-benzyl-4-(cyclohexylmethylamino)piperidine-4-carboxamide (8 g, 24.32 mmol), 8 ml of trimethoxymethane, 2 ml of acetic acid and 65 ml of toluene was refluxed for 48 hours. The mixture was concentrated. The residue was dissolved in water, made alkaline with aqueous ammonia, and the mixture was extracted with chloroform. The extracts were dried (MgSO$_4$) and concentrated. Recrystallization of the residue from ethyl acetate gave 6.3 g (76.5%) of crystals, mp 117°–118° C.

4. Preparation of 8-(t-Butoxycarbonyl)-1-cyclohexylmethyl-1,3,8-triazaspiro[4.5]decan-4-one ($\underline{5}$, R=c-CH$_6$H$_{11}$CH$_2$).

A mixture of 6 g (17.7 mmol) of 8-benzyl-1-cyclohexylmethyl-1,3,8-triazaspiro[4.5]dec-2-ene-4-one, 2 ml of concentrated hydrochloric acid, 70 ml of isopropanol, 50 ml of methanol and 1 g of 10% palladium-on-carbon was hydrogenated for 2 days on a Parr apparatus at an intital pressure of 50 psi of hydrogen. After being flooded with nitrogen the mixture was filtered and the filtrate was concentrated. The residue was taken into water and the solution was made alkaline by addition of an aqueous solution of sodium carbonate. The precipitated product was brought into solution by addition of 100 ml of isopropanol. Di-tert-butyl dicarbonate (4 g, 20 mmol) was added to the solution. After the resulting solution was stirred at 25° C. for 24 hours, it was concentrated to remove the isopropanol solvent and additional water was added. The mixture was extracted with ethyl acetate. The extracts were dried (MgSO$_4$) and concentrated. The residue was chromatographed (silica gel, 0 to 30% gradient of ethyl acetate in hexane) and the solid obtained after concentration of the eluent was recrystallized from hexane to give 4.5 g (72.5%) of crystals, mp 149°–151° C.

5. Preparation of Methyl 8-(t-Butoxycarbonyl)-1-cyclohexylmethyl-4-keto-1,3,8-trizaspiro[4.5]de 3-acetate 8, R=c-C$_6$H$_{11}$CH$_2$, D=CH$_2$, R$^3$=CH$_3$).

To a stirred solution of 8-(t-butoxycarbonyl)-1-(cyclohexylmethyl)-1,3,8-triazaspiro[4.5]decan-4-one (3.76 g, 10.7 mmol) in 50 ml of dimethylformamide at 0° C. under argon was added, in portions, 54 mg (13.3 mmol) of an 80% dispersion of sodium hydride in mineral oil. After the mixture was stirred for 30 minutes at 0° C., methyl bromoacetate (2 g) was added dropwise and stirring was continued for an additional 20 hours. The mixture was poured into 200 ml of water and extracted with ethyl acetate. After the extracts were dried over magnesium sulfate, they were concentrated. The residue was purified by column chromatography (silica gel, 0 to 30% gradient of ethyl acetate in hexane) to afford the product as 4.48 (88.3%) of a colorless liquid.

6. Preparation of 8-(t-Butoxycarbonyl)-1-cyclohexylmethyl-4-keto-1,3,8-triazaspiro[4.5]decan-3-acetic acid (9, R=c-C$_6$H$_{11}$CH$_2$, D=CH$_2$).

A stirred mixture of 4 g (9.45 mmol) of methyl 8-(t-butoxycarbonyl)-1-cyclohexylmethyl-4-keto-1,3,8-triazaspiro [4.5]decan-3-acetate, 4 g (72 mmol) carbonate 60 ml of methanol and 40 ml of water was heated at reflux for 3 hours. The resulting solution was concentrated to about one-half of its original volume and then it was carefully acidified with 2N HCl at 0° C. The resulting mixture was extracted with ethyl acetate. After the extracts were dried over magnesium sulfate, they were concentrated. The residue solid was recrystallized from hexane to give the product as 2.75 g (69.5%) of colorless crystals, mp 148°–149° C.

Example 4

Synthesis of 8-(t-Butoxycarbonyl)-1-cyclohexyl-4-keto-1,3,8-triazaspiro[4,5]decan-3-acetic Acid (9, R=c-C$_6$H$_{11}$ D=CH$_2$)

1→2(R=c-C$_6$H$_{11}$)→3(R=c-C$_6$H$_{11}$)→4(R=c-C$_6$H$_{11}$)

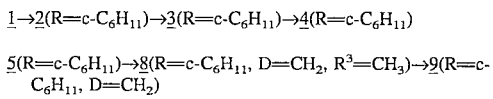

Employing cyclohexylamine as starting material, 8-(t-butoxycarbonyl)-1-cyclohexyl-4-keto-1,3,8-triazaspiro[4.5]-decan-3-acetic acid, colorless crystals, mp 173°–174° C. (from ethyl acetate-hexane), was obtained by the general route described in Example 3.

Example 5

Synthesis of 8-(t-Butoxycarbonyl)-4-keto-1-(4-methoxyphenyl)-1,3,8-triazaspiro[4.5]-decan-3-acetic Acid (9, R=4-CH$_3$OPh, B=CH$_2$)

1→2(R=4-CH$_3$OPh)→3(R=4-CH$_3$OPh)→4(R=4-CH$_3$OPh)

5(R=4-CH$_3$OPh)→8(R=4-CH$_3$OPh, D=CH$_2$, R$^3$=CH$_3$)→

9(R=4-CH$_3$OPh, D=CH$_2$)

Employing 4-methoxyaniline as starting material 8-(t-butoxycarbonyl)-4-keto-1-(4-methoxyphenyl)-1,3,8-triazaspiro[4.5]decan-3-acetic acid was produced as colorless crystals, mp 173°–174° C., by the general route detailed in Example 3.

Intermediates 2–8 indicated above were isolated as follows:

1-benzyl-4-cyano-4-(4-methoxylanilino)piperidine, mp 116°–118° C. (from 1:1 cyclohexane/isopropanol), 79.1% yield;

1-benzyl-4-(4-methoxyanilino)piperidine-4-carboxamide, mp 131°–135° C. (from isopropanol), 82.9% yield;

8-benzyl-1-(4-methoxyphenyl)-1,3,8-triazaspiro[4.5]dec-2-ene-4-one, mp 194°–197° C. (ether trituration), 84.7% yield;

8-(t-butoxycarbonyl)-1-(4-methoxyphenyl)-1,3,8-triazaspiro[4.5]decan-4-one, mp 188°–190° C. (from methanol), 53.0% yield; and methyl 8-(t-butoxycarbonyl)-4-keto-1-(4-methoxyphenyl)-1,3,8-triazaspiro[4.5]decan-3-acetate, mp 94°–97° C. (chromatography, silica, methanol-methylene chloride, 1 to 5% methanol gradient), 94.8% yield.

Example 6

Synthesis of 8-(t-Butoxycarbonyl)-1-(n-propyl)-4-keto-1,3,8-triazaspiro[4.5]decan-3-acetic Acid (9.R=n-Pr. B=CH$_2$)

3(R=n-Pr)→4(R=n-Pr)→5(R=n-Pr)→8(R=n-Pr, D=CH$_2$, R$^3$=CH$_3$)→9(R=n-Pr, D=CH$_2$)

1. Preparation of 8-Benzyl-1-(n-propyl)-1,3,8-triazaspiro[4.5]dec-2-ene-4-one(4, (R=n-Pr).

A stirred mixture of 10 g (36.4 mmol) of 1-benzyl-4-[N-(n-propyl)amino]piperidine-4-carboxamide (Aldrich Chemical Co., Inc., Milwaukee, Wis.), 2 ml of trimethoxymethane, 5 ml of acetic acid and 30 ml of toluene was refluxed for 48 hours. After the reaction mixture was cooled to 25° C., it was diluted with 100 ml of water and 100 ml of chloroform. The mixture was basified with aqueous ammonia and the chloroform layer was separated. The aqueous layer was extracted three times with 50 ml portions of chloroform. The combined chloroform solutions were dried over sodium sulfate and concentrated in vacuo. The residue was recrystallized from isopropanol to give 7.78 g (75%) of product as crystals, mp 146°–150° C.

2. Preparation of 8-(t-Butoxycarbonyl)-1-(n-propyl)-1,3, 8-triazaspiro[4.5]decan-4-one(5, R =n-Pr).

A mixture of (7.25 g, 25.4 mmol) of 8-benzyl-1-(n-propyl)-1,3,8-triazaspiro[4.5]dec-2-ene-4-one, 50 ml of methanol, 50 ml of isopropanol, 3 ml of concentrated hydrochloric acid and 2 g of 10% palladium-on-carbon was shaken on a Parr shaker at 25° C. under an initial atmosphere of 45 psi of hydrogen for 2 days. After the mixture was flooded with nitrogen, it was filtered and the filtrate was concentrated. The residue was dissolved in water and the resulting solution was basified with 2N NaOH. The mixture was extracted with chloroform. After the extracts were dried over anhydrous sodium sulfate, they were concentrated in vacuo. The residue was dissolved in 40 ml of dioxane. The solution was cooled to 0° C. and 6.55 g (30 mmol) of di-tert-butyl dicarbonate was added. After the mixture was stirred at 25° C. for 20 hours, it was diluted with 100 ml of water. The mixture was extracted with ether. After the extracts were dried over anhydrous sodium sulfate, they were concentrated under reduced pressure. The residue was chromatographed on a column of silica gel, eluting with methanol-methylene chloride (1 to 20% methanol gradient) to provide 2.95 g (39%) of crystalline product, mp 110°–113° C.

3. Preparation of Methyl 8-(t-Butoxycarbonyl)-4-keto-1-(n-propyl)-1,3,8-triazaspiro[4.5]decan-3-acetate (8, R=n-Pr, D=CH$_2$, R$^3$=CH$_3$).

To a stirred solution of 1.51 g (5.1 mmol) of 8-(t-butoxycarbonyl)-1-(n-propyl)-1,3,8-triazaspiro[4.5]decan-4-one in 25 ml of dimethylformamide at 0° C. under argon was added, in portions 0.24 g (6 mmol) of a 60% dispersion of sodium hydride in mineral oil. After the mixture was stirred for 30 minutes at 0° C., 0.92 g (6 mmol) of methyl bromoacetate was added dropwise. The mixture was then stirred at 25° C. for 6 hours. After the mixture was diluted with 100 ml of water, it was extracted with ethyl acetate. The extracts were washed with water and brine, dried over anhydrous sodium sulfate, and concentrated in vacuo. The residue was chromatographed on a column of silica gel, eluting with methanol-methylene chloride (1 to 5% methanol gradient) to provide the product (1.84 g, 98.2%) as a colorless liquid.

4. Preparation of 8-(t-Butoxycarbonyl)-1-(n-propyl)-4-keto-1,3,8-triazaspiro[4.5]decan-3-acetic Acid (9, R=n-Pr, D=CH$_2$).

A stirred mixture of 1,80 g (4.87 mmol) of methyl 8-(1-butoxycarbonyl)-4-keto-1- (n-propyl)-1,3,8-triazapiro [4.5]decan-3-acetate, 1.3 g of sodium carbonate, 30 ml of methanol and 20 ml of water was heated under reflux for 3 hours. The resulting solution was concentrated to about one-half of its original volume, cooled to 0° C. and carefully acidified with concentrated hydrochloric acid. The mixture was extracted with ethyl acetate. The extracts were washed with water, then brine, dried over anhydrous sodium sulfate, and concentrated under reduced pressure. Recrystallization of the residue from 95% ethanol gave 1.22 g (70.5%) of the product as a solid, mp 180°–182° C. (dec).

Example 7

Synthesis of 8-(t-Butoxycarbonyl)-4-keto-1-(4-methylphenyl)-1,3,8-triazaspiro[4.5]decan-3-acetic Acid (9, R=4-CH$_3$Ph, B=CH$_2$ 3(R=CH$_3$Ph)→6(R=4-CH$_3$Ph)→7(R=4-CH$_3$Ph, D=CH$_2$, R$^3$=Bn)→9(R=4-CH$_3$Ph, D=CH$_2$)

1. Preparation of 8-Benzyl-1-(4-methylphenyl)-1,3,8 triazaspiro[4.5]decan-4-one (6, R=4-CH$_3$Ph).

A mixture of 3.23 g (10 mmol) of 1-benzyl-4-(p-toluidino)isonipecotamide (Aldrich Chemical Co., Inc., Milwaukee, Wis.) and 1.035 g (23 mmol) of formamide was heated at 210° C. for 2 hours. The mixture was cooled to ambient temperature and 100 ml of water was added. After the resulting mixture was basified with saturated aqueous ammonia, it was extracted with chloroform. The extracts were dried over anhydrous potassium carbonate and concentrated. Recrystallization of the solid residue from ethyl acetate afforded 2.67 g (79.2%) of the product as colorless crystals, mp 212°–213° C.

2. Preparation of Benzyl 8-Benzyl-4-keto-1,3,8-triazaspiro[4.5]decan-3-acetate (7, R=4-CH$_3$Ph, D=CH$_2$, R$_3$=Bn).

To a stirred solution of 0.7 g (2.08 mmol)of 8-benzyl-1-(4-methylphenyl)-1,3,8triazaspiro[4.5]decan-4-one in 20 ml of dry dimethylformamide at 0° C. under argon was added, in portions, 0.075 g (2.49 mmol) of an 80% dispersion of sodium hydride in mineral oil. After the mixture was stirred for 30 minutes, 0.71 g (3.1 mmol) of benzyl bromoacetate was added dropwise at 0° C. The resulting mixture was stirred at 25° C. for 20 hours, then 50 ml of water was added. The mixture was extracted with ethyl acetate. After the extracts were washed with water, they were dried over anhydrous sodium sulfate, and concentrated in vacuo. The residue was chromatographed on a silica gel column, eluting with ethyl acetate-hexane (0 to 60% gradient) to afford 0.66 g (66%) of the product as a yellow oil.

3. Preparation of 8-(t-Butoxycarbonyl)-4-keto-1-(4-methylphenyl)-1,3,8-triazaspiro[4.5]decan-3-acetic Acid (9, R=4-CH$_3$Ph, D=CH$_2$).

A mixture of 0.9 g (1.86 mmol) of benzyl 8-benzyl-4-keto-1,3,8-triazaspiro[4.5]decan-3-acetate, 0.81 g (3.72 mmol) of di-tert-butyl dicarbonate, 25 ml of methanol, 25 ml of ethyl acetate, and 100 mg of 10% palladium-in-carbon was shaken on a Parr apparatus under an initial pressure of 60 psi of hydrogen for 4 hours, until TLC (silica, ethyl acetate) indicated complete reaction. The mixture was flooded with nitrogen, filtered and the filtrate was concentrated under reduced pressure. Recrystallization of the residual solid from ethyl acetate-hexane gave 0.56 g (74.7%) of the product as colorless crystals, mp 173°–175° C.

Example 8

Peptide Synthesis

The pseueopeptides listed in Table I were synthesized manually using standard solid phase methods and t-Boc chemistry by the following procedures.

1. Boc-Arg(Tos)-PAM resin was used for the purpose. Amino acids and the Boc-protected derivatives of substituted 4-keto-1,3,8-triazaspiro[4.5]decan-3-alkanoic acid prepared in Examples 1–7 were introduced according to the sequence of the pseudopeptide.

2. Deprotection: The N-terminal t-Boc protection was accomplished by treating the resin-aa/resin-peptide with trifluoroacetic acid/methylene chloride (1:1) for two minutes followed by a similar treatment for 30 minutes.

3. The resin was then washed with methylene chloride and ethanol and neutralized with 10% triethylamine/methylene chloride or 10% diisopropylethylamine/methylene chloride.

4. Couplings: All couplings were carried out using the active ester of the amino acid. The active esters of the individual amino acids were generated prior to their introduction into solid phase synthesis. Five equivalents (with respect to loading of the first amino acid on the resin) of the amino acid, hydroxybenzotriazole hydrate and dicyclohexycarbodiimide or diisopropylcarbodiimide, was incubated for 30 minutes at 0° C. in dimethyl formamide or methylene chloride/dimethyl formamide (1:1) for this purpose. Couplings were followed until no more free amine was detected on the resin using qualitative ninhydrin analysis (kaiser test). Different unnatural amino acids behave differently during ninhydrin analysis and the color of the resin (after deprotection and coupling) depends on the specific amino acid being used.

5. After coupling, the resin-peptide was washed with dimethyl formamide and methylene chloride before commencement of another cycle of the synthesis.

6. The finished peptidyl-resin was cleaved from the resin using HF (10mL/g of resin) in the presence of 10% anisole (scavenger). After removal of HF, the peptide resin was washed with ether and the peptide was extracted with 0.1% TFA or 0.2% acetic acid. Lyophilization yielded crude peptide, usually flaky yellow solids were obtained at this stage.

7. The crude peptide was purified using reverse phase high performance liquid chromatography on a $C_{18}$ column using a gradient of water/acetonitrile (both containing 0.1% trifluoroacetic acid or 0.2% acetic acid). The pure fractions were determined by analytical HPLC, on a Vydac $C_{18}$ column using a gradient of water/acetonitrile (both containing 0.1% trifluoroacetic acid) and pooled together and lyophilized to give flaky white solids.

8. Peptides were analyzed by analytical reverse phase HPLC on a Vydac $C_{18}$ column using a gradient of water/acetonitrile (both containing 0.1% trifluoroacetic acid), and fast atom bombardment mass spectroscopy.

Example 9

Human Bradykinin Receptor Binding

The human bradykinin $B_2$ receptor was cloned by Hess et al. (*Biochem. Biophys. Res. Comm.*, (1992), 184, 260–268). A human bradykinin $B_2$ receptor was expressed in CHO/K cells. Briefly, approximately $2 \times 10^6$ plaques from a human uterus λ gt10 cDNA library (Clontech Laboratories; Palo Alto, Calif.) were screened using a PCR fragment containing the coding region of the rat $B_2$ receptor. This probe was generated by random-primed synthesis in the presence of α [$^{32}$P]dATP. Duplicate filters were hybridized overnight at 42° C. in 1M NaCl, 50 mM Tris pH 7.5, 5X Denhardt's, 200 µg/ml salmon sperm DNA, 1% SDS, and 20% formamide. The filters were washed at 65° C. in 1X SSC and 1% SDS. Coincident positively hybridizing plaques were purified and rescreened with the same probe and stringency conditions. EcoR I fragments of positive clones were inserted into Bluescript/KS II + vector (Stratagene; La Jolla, Calif.) for sequence determination.

The nucleotide sequence of the cloned human $B_2$ receptors was determined using double-stranded DNA and the dideoxy chain termination method. Commercially available T3 and T7 oligonucleotides (USB; Cleveland, Ohio) and synthetic 21-mer oligonucleotides (DNA/RNA Synthesizer, Applied Biosystems Inc.; Palo Alto, Calif.) from both the known rat sequence and the determined human sequence were used to identify the nucleotide sequence from the 5' untranslated end to the Bgl II site in the 3' untranslated end of the clone. The Hind III/Xba I fragment of one full-length clone, 126A, was inserted into pcDNA I neo vector (Invitrogen; San Diego, Calif.) for expression in mammalian cell lines.

CHO/K cells were plated in 2 ml of growth medium (Ham's F12 with 10% FBS) per 6 well plate and incubated at 37° C., 5% $CO_2$ until they were 60% confluent. For each well, 4, 12, and 16 µg of DNA was diluted in 100 µl Opti-MEM I reduced serum medium (Gibco/BRL; Gaithersburg, Md.). 12 µl of TransfectASE reagent (Gibco/BRL) was diluted in a separate aliquot of 100 µl Opti-MEM I. The DNA and TransfecASE solutions were combined, mixed gently, and incubated at 25° C. for 15 minutes. This solution was then diluted to 1 ml with Opti-MEM I. Each well was washed twice with Opti-MEM I and 1 ml of the DNA/TransfectAse complex was added to each well. After a 5 hour incubation at 37° C. and 5% $CO_2$, 1 ml of Ham's F12 with 20% FBS was added to each well and cells were incubated overnight. Media was replaced with growth medium and incubated for additional 24 hours.

Cells were harvested by trypsinization and replated in selection medium (Ham's F12, 10% FBS and 500 µg/ml Geneticin (Gibco/BRL). Media was replaced every 48 hours for 2 weeks. Any colonies remaining after selection were transferred to separate 10 cm dishes, grown to confluency and positive clones were determined by binding of 3H-NPC 17731 a bradykinin antagonist peptide described by Burch et al., (DuPont Biotech update, 1992;4:127–140). Colonies expressing the receptor were put out at limiting dilution. Cells were expanded and positive clones were identified as above. A cell line designated H2O.2 was used to quantitate binding of the compounds of the invention to the human bradykinin $B_2$ receptor.

Radioligand Binding Assays

H2O.2 cells were grown to confluency in Ham's F12 media containing 10% FBS and 500 µg/ml Geneticin. Growth media was aspirated and the monolayer washed once with Dulbecco's PBS without $Ca^{++}$ and $Mg^{++}$. Cells were scraped in Dulbecco's PBS and centrifuged at 2000 ×g for 10 minutes. Pellets were resuspended in 25 mM TES, 1 mM 1,10-phenanthroline pH 6.8 buffer and homogenized using a Ploytron at setting 5 for 10 seconds. An aliquot was taken for a protein determination using a BioRad protein assay kit. Membranes were centrifuged at 48000 ×g for 10 minutes at 4° C. Pellets were resuspended in the TES buffer with 0.1% BSA and 0.014% bacitracin. 0.5 ml aliquots were frozen in liquid $N_2$ and stored at –80° C. for up to 2 weeks.

Membranes from H2O.2 cells previously prepared were thawed at 37° C. and diluted in 25 mM TES, 1 µM 1,10-phenanthroline pH 6.8 containing BSA and bactiracin. For saturation binding assays, increasing concentrations of 3H-bradykinin or $^3$H-NPC 17731 were incubated with 16.5 µg of membrane protein in a total volume of 3 ml of the same buffer. Non-specific binding was determined with 1 µM bradykinin. The tubes were incubated 90 minutes at 25° C. and the assay was terminated by rapid vacuum filtration onto Whatman GF/B filters presoaked with 0.2% PEI for 3 hours followed by 2×3 ml aliquots of ice-cold 50 mM Tris, pH 7.4.

Radioactivity was counted with a Beckman scintillation counter. The test results obtained are shown in Table I.

Example 10

Determination of Bradykinin Antagonist Activity

The following protocol was designed to identify compounds that possess antagonist activity at bradykining receptors on intestinal (ileal longitudinal) smooth muscle.

Guinea pig intestine was removed and placed in a Petri dish containing Tyrodes solution and cut into 3–4 cm segments. The longitudinal muscle was separated from the underlying circular muscle using a cotton applicator (Paton and Zar, *J. Physiol.*, (1968), 194:13. Muscle strips were connected to isometric force-displacement transducers (Grass or Gould) coupled to a physiograph and placed in tissue baths containing Tyrode's solution at 37° C. Each preparation was suspended under a resting tension of 2 g.

After equilibration of the tissues, appropriate volumes of bradykinin solutions were cumulatively added to the 10 ml tissue baths to increase the concentration of bradykinin in the bath step-by-step without washing out after each single dose. Higher concentrations were added only after the preceding contraction had reached a steady value. When the next concentration step did not cause a further increase in contraction, it was assumed that the maximum effect had been obtained and the tissue was washed to remove bradykinin and allowed to recover for 15 minutes. Antagonism of bradykinin responses to the presence of antagonist were determined by repeating the cumulative addition procedure for bradykinin after the tissue has been exposed to the antagonist for 5 minutes. Three or four different concentrations of antagonist were studied sequentially in the same preparations. Responses were expressed as a percentage of the maximum contraction elicited by bradykinin in the absence of antagonist. $pA_2$ values were calculated by Schild analysis. Results are tabulated in Table I.

The invention being thus described, it will be obvious that the same may be varied in many ways. Such variations are not to be regarded as a departure from the spirit and scope of the invention and all such modifications are intended to be included within the scope of the following claims.

TABLE I

| NPC | Test Compound | $K_i$ (nM) | $pA_2$ |
|---|---|---|---|
| 18521 | H—D—Arg—Arg—X[Ph]—CH$_2$CO—Ser—D—Tic—Oic—Arg—OH | 7.7 | 6.70 |
| 18609 | H—D—Arg—Arg—X[4-CH$_3$Ph]—CH$_2$CO—Ser—D—Tic—Oic—Arg—OH | 6.3 | |
| 18640 | H—D—Arg—Arg—X[c-C$_6$H$_{11}$CH$_2$]—CH$_2$CO—Ser—D—Tic—Oic—Arg—OH | 6.8 | |
| 18688 | H—D—Arg—Arg—X[c-C$_6$H$_{11}$]—CH$_2$CO—Ser—D—Tic—Oic—Arg—OH | 0.73 | 6.40 |
| 18677 | H—D—Arg—Arg—X[n-Pr]—CH$_2$CO—Ser—D—Tic—Oic—Arg—OH | 27 | 5.80 |
| — | H—D—Arg—Arg—X[4-CH$_3$OPh]—CH$_2$CO—Ser—D—Tic—Oic—Arg—OH | — | |
| 18637 | H—D—Arg—Arg—X[Ph]—CH$_2$CO—Ala—D—Tic—Oic—Arg—OH | 18.6 | |
| 18587 | H—D—Arg—Arg—X[Ph]—CH$_2$CO—Gly—D—Tic—Oic—Arg—OH | 66 | |
| 18586 | H—D—Arg—Arg—X[Ph]—CH$_2$CO—N—BnGly—D—Tic—Oic—Arg—OH | 54 | |
| 18645 | H—D—Arg—Arg—X[Ph]—CH$_2$CO—N—BnGly—Ser—D—Tic—Oic—Arg—OH | 31 | |
| 18589 | H—D—Arg—Arg—X[Ph]—(CH$_2$)$_4$CO—D—Tic—Oic—Arg—OH | 111 | |

We claim:

1. A pseudopeptide which has an affinity for a bradykinin receptor having the formula:

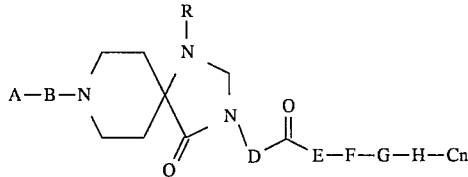

wherein,

A is selected from the group consisting of the L-and D-isomers of Arg and Lys;

B is selected from the group consisting of the L-and D-isomers of Arg and Lys;

R is selected from the group consisting of a straight, branched, saturated or unsaturated lower alkyl chain of 1 to 6 carbon atoms, a cycloalkyl or cycloalkylmethyl moiety in which the cyclalkyl ring comprises 3 to 6 carbon atoms, an aralkyl group, or an aryl group, wherein the aryl group is optionally substituted with a $C_1$–$C_4$ alkyl group, a $C_1$–$C_4$ alkoxy group, or a halogen;

D is a saturated or unsaturated alkylene bridging group consisting of 1 to 8 carbon atoms;

E is a direct bond or selected from the group consisting of Ser, Thr, Gly and Val;

F is selected from the group consisting of a D-Phe, D-Tic and D-trans-Hype, wherein an aryl or aralkyl group, if present in Hype, is selected from the group consisting of a phenyl, naphthyl, benzyl, and naphthylmethyl group;

G is selected from the group consisting of Oic, Aoc, Phe, Tic, and a Hype, wherein an aryl or a aralkyl group, if present in Hype, is selected from the group consisting of a phenyl, naphthyl, benzyl, and naphthylmethyl group;

H is selected from the group consisting of Arg and Lys;

Cn is selected from the group consisting of a hydroxyl group, an amino group, and an alkoxy group;

and pharmaceutically accepted salts thereof.

2. A pseudopeptide of claim 1 wherein:

A is D-Arg;

B is Arg;

R is selected from the group consisting of a straight, branched, saturated or unsaturated lower alkyl chain of 1 to 6 carbon atoms, a cycloalkyl or cyclolakylmethyl moiety in which the cyclalkyl ring comprises 3 to 6 carbon atoms, an aralkyl group, or an aryl group, wherein the aryl group is optionally substituted with a $C_1$–$C_4$ alkyl group, a $C_1$–$C_4$ alkoxy group, or a halogen;

D is a saturated or unsaturated alkylene bridging group consisting of 1 to 8 carbon atoms;

E is a direct bond or is selected from the group consisting of Ser and Gly;

F is selected from the group consisting of a D-Phe, D-Tic and D-trans-Hype, wherein an aryl or aralkyl group, if present in Hype, is selected from the group consisting of a phenyl, naphthyl, benzyl, and naphthylmethyl group;

G is selected from the group consisting of Oic, Aoc, Phe, Tic, and a Hype, wherein an aryl or aralkyl group, if present in Hype, is selected from the group consisting of a phenyl, naphthyl, benzyl, and naphthylmethyl group;

H is Arg;

Cn is selected from the group consisting of a hydroxyl group, an amino group, and an alkoxy group.

3. A pseudopeptide of claim 2 wherein:

A is D-Arg;

B is Arg;

R is selected from the group consisting of phenyl, 4-methylphenyl, 4-methoxyphenyl, 4-fluorophenyl, 4-chlorophenyl, benzyl, 1-naphthyl, 2-naphthyl, cyclohexyl, cyclohexylmethyl, n-propyl, n-pentyl, and neopentyl;

D is a saturated or unsaturated alkylene bridging group consisting of 1 to 4 carbon atoms;

E is a direct bond or Ser;

F is selected from the group consisting of D-Phe, D-Tic, D-Hype (trans-propyl), D-Hype (trans-thiophenyl), D-Hype (trans-phenyl propyl), D-Hype (trans-2-methylbutyl), D-Hype (trans-ethyl) and D-Hype (trans-methyl);
G is Oic;
H is Arg; and
Cn is OH.

4. A pseudopeptide of claim 3 wherein:
A is D-Arg;
B is Arg;
R is selected from the group consisting of phenyl, 4-methylphenyl, cyclohexyl, cyclohexylmethyl, and n-propyl;
D is a saturated or unsaturated alkylene bridging group consisting of 1 to 4 carbon atoms;
E is a direct bond or Ser;
F is selected from the group consisting of D-Phe, D-Tic, D-Hype(trans-thiophenyl) and D-Hype(trans propyl);
G is Oic;
H is Arg; and
Cn is a hydroxyl group.

5. A peptide of claim 1

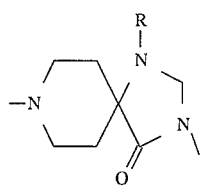

selected from the group consisting of:

H-D-Arg—Agr-X[Ph]-CH$_2$CO-Ser-D-Tic-Oic-Arg-OH
H-D-Arg—Agr-X[4-CH$_3$Ph]-CH$_2$CO-Ser-D-Tic-Oic-Arg-OH
H-D-Arg—Agr-X[4-CH$_3$OPh]-CH$_2$CO-Ser-D-Tic-Oic-Arg-OH
H-D-Arg—Agr-X[4-FPh]-CH$_2$CO-Ser-D-Tic-Oic-Arg-OH
H-D-Arg—Agr-X[4-ClPh]-CH$_2$CO-Ser-D-Tic-Oic-Arg-OH
H-D-Arg—Agr-X[1-naphthyl]-CH$_2$CO-Ser-D-Tic-Oic-Arg-OH
H-D-Arg—Agr-X[2-naphthyl]-CH$_2$CO-Ser-D-Tic-Oic-Arg-OH
H-D-Arg—Agr-X[Bn]-CH$_2$CO-Ser-D-Tic-Oic-Arg-OH
H-D-Arg—Agr-X[(CH$_2$)$_2$CH$_3$]-CH$_2$CO-Ser-D-Tic-Oic-Arg-OH
H-D-Arg—Agr-X[(CH$_2$)$_4$ CH$_3$]-CH$_2$CO-Ser-D-Tic-Oic-Arg-OH
H-D-Arg—Agr-X[CH$_2$C(CH$_3$)$_3$]-CH$_2$CO-Ser-D-Tic-Oic-Arg-OH
H-D-Arg—Agr-X[c-C$_6$H$_{11}$]-CH$_2$CO-Ser-D-Tic-Oic-Arg-OH
H-D-Arg—Agr-X[c-C$_6$H$_{11}$CH$_2$]-CH$_2$CO-Ser-D-Tic-Oic-Arg-OH
H-D-Arg—Agr-X[Ph]-CH$_2$CO-Ser-D-Hype( trans SPh )-Oic-Arg-OH
H-D-Arg—Agr-X[4-CH$_3$Ph]-CH$_2$CO-Ser-D-Hype(trans SPh)-Oic-Arg-OH
H-D-Arg—Agr-X[4-CH$_3$OPh ]-CH$_2$CO-Ser-D-Hype-(trans SPh) -Oic-Arg-OH
H-D-Arg—Agr-X[4-FPh]-CH$_2$CO-Ser-D-Hype(trans SPh)-Oic-Arg-OH
H-D-Arg—Agr-X[4-ClPh]-CH$_2$CO-Ser-D-Hype( trans SPh )-Oic-Arg-OH
H-D-Arg—Agr-X[1-naphthyl]-CH$_2$CO-Ser-D-Hype-(trans SPh)-Oic-Arg-OH
H-D-Arg—Agr-X[2-naphthyl]-CH$_2$CO-Ser-D-Hype( trans SPh )-Oic-Arg-OH
H-D-Arg—Agr-X[Bn]-CH$_2$CO-Ser-D-Hype(trans SPh)-Oic-Arg-OH
H-D-Arg—Agr-X[(CH$_2$)$_2$CH$_3$]-CH$_2$CO-Ser-D-Hype-(trans SPh)-Oic-Arg-OH
H-D-Arg—Agr-X[(CH$_2$)$_4$ CH$_3$]-CH$_2$CO-Ser-D-Hype-(trans SPh)-Oic-Arg-OH
H-D-Arg—Agr-X[CH$_2$C(CH$_3$)$_3$]-CH$_2$CO-Ser-D-Hype-(trans SPh)-Oic-Arg-OH
H-D-Arg—Agr-X[c-C$_6$H$_{11}$]-CH$_2$CO-Ser-D-Hype(trans SPh )-Oic-Arg-OH
H-D-Arg—Agr-X[c-C$_6$H$_{11}$CH$_2$]-CH$_2$CO-Ser-D-Hype-(trans SPh)-Oic-Arg-OH
H-D-Arg—Agr-X[Ph]-CH$_2$CO-Ser-D-Hype( trans n-Pr)-Oic-Arg-OH
H-D-Arg—Agr-X[4-CH$_3$Ph]-CH$_2$CO-Ser-D-Hype(trans n-Pr)-Oic-Arg-OH
H-D-Arg—Agr-X[4-CH$_3$OPh]-CH$_2$CO-Ser-D-Hype-(trans n-Pr)-Oic-Arg-OH
H-D-Arg—Agr-X[4-FPh]-CH$_2$CO-Ser-D-Hype(trans n-Pr)-Oic-Arg-OH
H-D-Arg—Agr-X[4-ClPh]-CH$_2$CO-Ser-D-Hype(trans n-Pr)-Oic-Arg-OH
H-D-Arg—Agr-X[1-naphthyl]-CH$_2$CO-Ser-D-Hype-(trans n-Pr)-Oic-Arg-OH
H-D-Arg—Agr-X[2-naphthyl]-CH$_2$CO-Ser-D-Hype-(trans n-Pr)-Oic-Arg-OH
H-D-Arg—Agr-X[Bn]-CH$_2$CO-Ser-D-Hype(trans n-Pr)-Oic-Arg-OH
H-D-Arg—Agr-X[(CH$_2$)$_2$CH$_3$]-CH$_2$CO-Ser-D-Hype-(trans n-Pr)-Oic-Arg-OH
H-D-Arg—Agr-X[CH$_2$C(CH$_3$)$_3$]-CH$_2$CO-Ser-D-Hype-(trans n-Pr)-Oic-Arg-OH
H-D-Arg—Agr-X[c-C$_6$H$_{11}$]-CH$_2$CO-Ser-D-Hype(trans n-Pr)-Oic-Arg-OH
H-D-Arg—Agr-X[c-C$_6$H$_{11}$CH$_2$]-CH$_2$CO-Ser-D-Hype-(trans n-Pr)-Oic-Arg-OH
H-D-Arg—Agr-X[Ph]-CH$_2$CO-N-BnGly-D-Tic-Oic-Arg-OH
H-D-Arg—Agr-X[Ph]-CH$_2$CO-N-BnGly-D-Hype(trans SPh)-Oic-Arg-OH
H-D-Arg—Agr-X[Ph]-CH$_2$CO-N-BnGly-D-Hype(trans n-Pr)-Oic-Arg-OH
H-D-Arg—Agr-X[c-C$_6$H$_{11}$CH$_2$]-CH$_2$CO-N-BnGly-D-Tic-Oic-Arg-OH
H-D-Arg—Agr-X[c-C$_6$H$_{11}$CH$_2$]-CH$_2$CO-N-BnGly-D-Hype(trans S Ph)-Oic-Arg-OH
H-D-Arg—Agr-X[c-C$_6$H$_{11}$CH$_2$]-CH$_2$CO-N-BnGly-D-Hype(trans n-Pr)-Oic-Arg-OH
H-D-Arg—Agr-X[Ph]-(CH$_2$)$_4$ CO-D-Tic-Oic-Arg-OH
H-D-Arg—Agr-X[Ph]-(CH$_2$)$_4$CO-D-Hype(trans SPh)-Oic-Arg-OH
H-D-Arg—Agr-X[Ph]-(CH$_2$)$_4$CO-D-Hype(trans n-Pr)-Oic-Arg-OH
H-D-Arg—Agr-X[c-C$_6$H$_{11}$CH$_2$]-(CH$_2$)$_4$CO-D-Tic-Oic-Arg-OH H-D-Arg—Agr-X[c-C$_6$H$_{11}$CH$_2$]-(CH$_2$)$_4$ CO-D-Hype-(trans SPh)-Oic-Arg-OH H-D-Arg—Agr-X[c-C$_6$H$_{11}$CH$_2$]-(CH$_2$)$_4$CO-D-Hype-(trans n-Pr)-Oic-Arg-OH H-D-Arg—Agr-X[Ph]-CH$_2$CH=CH-CH$_2$CO-D-Tic-Oic-Arg-OH H-D-Arg—Agr-X[Ph]-CH$_2$CH=CH-CH$_2$CO-D-Hype-(trans SPh)-Oic-Arg-OH H-D-Arg—Agr-X[Ph]-CH$_2$CH=CH-CH$_2$CO-D-Hype-(trans n-Pr)-Oic-Arg-OH H-D-Arg—Agr-X[c-C$_6$H$_{11}$CH$_2$]-CH$_2$CH=CH CH$_2$CO-D-Tic-Oic-Arg-OH H-D-Arg—Agr-X[c-C$_6$H$_{11}$CH$_2$]-CH$_2$CH=CH CH$_2$CO-D-Hype(trans SPh)-Oic-Arg-OH H-D-Arg—Agr-X[c-C$_6$H$_{11}$CH$_2$]-CH$_2$CH=CH CH$_2$CO-D-Hype(trans n-Pr)-Oic-Arg-OH H-D-Arg—Agr-X[Ph]-CH$_2$CH$_2$C[(CH$_2$)$_2$]CH$_2$CO-D-Tic-Oic-Arg-OH H-D-Arg—Agr-X[Ph]-CH$_2$CH$_2$C[(CH$_2$)$_2$]CH$_2$CO-D-Hype(trans SPh)-Oic-Arg-OH H-D-Arg—Agr-X[Ph]-CH$_2$CH$_2$C[(CH$_2$)$_2$]CH$_2$CO-D-Hype(trans n-Pr)-Oic-Arg-OH H-D-Arg—Agr-X[Ph]-CH$_2$CO-Ala-D-Tic-Oic-Arg-OH H-D-Arg—Agr-X[Ph]-CH$_2$CO-Ala-D-Hype(trans SPh)-Oic-Arg-OH H-D-Arg—Agr-X[Ph]-CH$_2$CO-Ala-D-Hype(trans n-Pr)-Oic-Arg-OH H-D-Arg—Agr-X[c-C$_6$H$_{11}$CH$_2$]-CH$_2$CO-Ala-D-Tic-Oic-Arg-OH H-D-Arg—Agr-X[c-C$_6$H$_{11}$CH$_2$]-CH$_2$CO-Ala-D-Hype-(trans SPh)-Oic-Arg-OH H-D-Arg—Agr-X[c-C$_6$H$_{11}$CH$_2$]-CH$_2$CO-Ala-D-Hype-(trans n-Pr)-Oic-Arg-OH H-D-Arg—Agr-X[Ph]-CH$_2$CO-Gly-D-Tic-Oic-Arg-OH H-D-Arg—Agr-X[Ph]-CH$_2$CO-Gly-D-Hype(trans SPh)-Oic-Arg-OH H-D-Arg—Agr-X[Ph]-CH$_2$CO-Gly-D-Hype(trans n-Pr)-Oic-Arg-OH H-D-Arg—Agr-X[c-C$_6$H$_{11}$CH$_2$]-CH$_2$CO-Gly-D-Tic-Oic-Arg-OH H-D-Arg—Agr-X[c-C$_6$H$_{11}$CH$_2$]-CH$_2$CO-Gly-D-Hype-(trans SPh)-Oic-Arg-OH H-D-Arg—Agr-X[c-C$_6$H$_{11}$CH$_2$]-CH$_2$CO-Gly-D-Hype-(trans n-Pr)-Oic-Arg-OH wherein X is the group:

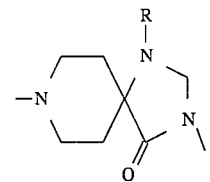

and the substituent R is described in brackets [R].

6. A pharmaceutical composition useful as a bradykinin receptor antagonist comprising a pharmaceutically acceptable carrier and a peptide of claim 1 in an amount effective to antagonize bradykinin.

7. A pharmaceutical preparation for treating local pain and inflammation from burns, wounds, cuts, rashes or other trauma and pathological conditions caused by the production of bradykinin or related kinins by an animal, which comprises a peptide of claim 1 in an amount effective to antagonize bradykinin, together with a pharmaceutically acceptable carrier.

* * * * *